United States Patent [19]

Nutter et al.

[11] Patent Number: 4,559,308
[45] Date of Patent: Dec. 17, 1985

[54] CORYNEBACTERIUM PLASMID AND VECTOR

[75] Inventors: Robert C. Nutter, El Cerrito; Lucy C. Panganiban, San Francisco, both of Calif.

[73] Assignee: Stauffer Chemical Co., Westport, Conn.

[21] Appl. No.: 461,364

[22] Filed: Jan. 27, 1983

[51] Int. Cl.[4] .................. C12N 1/00; C12N 15/00
[52] U.S. Cl. .......................... 435/317; 435/172.3; 935/29
[58] Field of Search ............ 435/172.3, 317, 843, 435/253; 935/22, 27

[56] References Cited

U.S. PATENT DOCUMENTS 3,220,929 11/1965 Kinoshita et al. .................. 435/110
4,500,640 2/1985 Katsumata et al. ............. 435/317 X

FOREIGN PATENT DOCUMENTS 0058889 9/1982 European Pat. Off. .
0063763 11/1982 European Pat. Off. .
0073062 3/1983 European Pat. Off. .
0078537 5/1983 European Pat. Off. ............ 435/317
2076853 12/1981 United Kingdom ............. 435/172.3

Primary Examiner—Thomas G. Wiseman
Assistant Examiner—Jayme A. Huleatt
Attorney, Agent, or Firm—Joel G. Ackerman; Leona L. Lauder; Elliott L. Fineman

[57] ABSTRACT

Plasmids derived from *Corynebacterium glutamicum*, particularly pRN3.1, of suitable size, about 3.1 kilobases in length and weight about $2.0 \times 10^6$ daltons, and having a limited number of restriction sites therein, suitable as vehicles for genetic engineering of Corynebacterium.

1 Claim, 1 Drawing Figure

CORYNEBACTERIUM PLASMID AND VECTOR

FIELD OF THE INVENTION

The instant invention relates to plasmids and vectors derived from *Corynebacterium (C.) glutamicum* ATCC 39269, which is derived from *Corynebacterium glutamicum* ATCC 13058.

BACKGROUND OF THE INVENTION

*Corynebacterium glutamicum* and microorganisms belonging to the genus Corynebacterium have proven to be important in the industrial production of amino acids, including glutamic acid and lysine, and salts thereof including monosodium glutamate. Corynebacterium has, however, proved to be refractory to genetic engineering using recombinant dexoyribonucleic acid (DNA) techniques for lack of suitable Corynebacterium plasmids which can be modified by enzymatic means for use as vectors.

The usefulness of plasmids and modified plasmids as vectors has been repeatedly demonstrated *Escherichia coli* (*E. coli*), *Bacillus subtillis* and Actinomycetes, all of which have been successfully modified using plasmid-derived vectors from each of the respective organisms, to produce chemical substances which are useful. Such substances include antibiotics, enhanced amino acid production and various hormones from eukaryotic, and in particular mammalian, species. The usefulness of *Corynebacterium glutamicum*, which has been used in numerous large-scale industrial fermentation processes, can be vastly improved if a vector system suitable for use in this microorganism can be developed.

SUMMARY AND OBJECTS OF THE INVENTION

A group of plasmids have been isolated from *Corynebacterium glutamicum*. The plasmids have been characterized with respect to restriction sites therein and thus may be used as vectors for modification of Corynebacterium.

It is an object of the invention to isolate and characterize plasmids occurring in microorganisms of the genus Corynebacterium. It is another object of the invention to develop from such plasmids vectors which may be used to intentionally modify the genetic complement of microorganisms of the genus Corynebacterium and other microorganisms.

DESCRIPTION OF THE DRAWING

These and other objects of the invention will be more readily understood with reference to FIG. 1, a map depicting the restriction endonuclease cleavage sites for pRN3.1. pRN3.1 has an approximate length of 3.1 kilobases. The positions of the various restriction endonucleases are given as kilobase coordinates relative to the Bgl II site at 0:0/3.1.

DETAILED DESCRIPTION OF THE INVENTION pRN3.1 is derived from *Corynebacterium glutamicum*, on deposit with the American Type Culture Collection, under the accession number 39269. This strain is derived from Corynebacterium glutamicum ATCC 13058 and is available to the public upon the grant of a patent disclosing ATCC 39269 to the Assignee, the Stauffer Chemical Company, from the American Type Culture Collection located in Rockville, Md., U.S.A. The deposit is also available pursuant to the requirements of foreign patent laws of countries in which counterparts of the subject application have been filed. The availability of the deposit does not itself constitute a license to practice the subject invention in derrogation of patent or certificate of invention rights granted the Assignee by governmental action.

Figure 1:
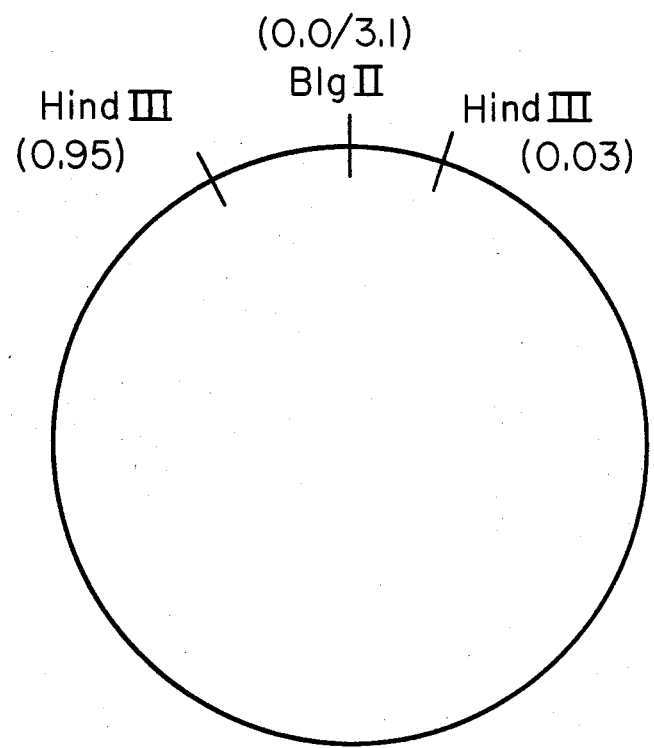

Colonies of *Corynebacterium glutamicum* ATCC 39269 were pre-cultured on 10 milliliters (ml) of tryptocase soy broth (TSB) (Difco). Replicates of the bacteria pre-culture were inoculated into one liter batches of minimal media with yeast extract (MMYE). Minimal media formulas appropriate for the growth of Corynebacterium are well known in the art. In the instant example, the medium was prepared as follows:

| MMYE Salts | Amount/l $H_2O$ |
| --- | --- |
| $(NH_4)_2SO_4$ | 200.0 g |
| NaCl | 2.0 g |
| $MgSO_4.7H_2O$ | 8.0 g |
| $FeSO_4.4-6\ H_2O$ | 0.04 g |
| $MnSO_4.4-6\ H_2O$ | 0.04 g |

| MMYE Buffer | Amount/l $H_2O$ |
| --- | --- |
| urea | 60.0 g |
| $KH_2PO_4$ | 20.0 g |
| biotin | 0.001 g |
| thiamine | 0.004 g |

MMYE medium is prepared by adding 50 ml of the sterile MMYE salt solution and 50 ml of sterile MMYE buffer solution to a sterile solution containing 900 ml $H_2O$, 20 grams (g) glucose, and one gram yeast extract.

The inoculated cultures were grown with shaking at approximately 200 rpm at 30° C. When the cells were well into, but not past log phase growth, and preferably at mid-log growth, indicated in the example by Klett measurement of approximately 50, penicillin G was added to each culture to a final concentration of one microgram (ug) per ml. After the addition of penicillin G, the culture was incubated with shaking at 30° C. for a sufficient period of time to ensure at least two divisions of the cells, in this example, about 2.5 hours.

The cells were harvested by centrifugation at 4° C. at a speed sufficient to pellet the cells. In this example, a Sorvell GS-3 rotor at about 6000 rpm was used, but, depending on culture volume, another rotor can be used equally as well.

The pellet was washed one time with an excess of 50 millimolar (mM) tris(hydroxymethyl)aminomethane (TRIS) buffer at pH 8 containing approximately 20 mM ethylenediaminetetracetic acid (EDTA). After washing, the cells were spun down in an appropriate centrifuge and were stored overnight at −20° C. The freezing step may, however, be dispensed with when it is desirable to proceed directly to the isolation of the plasmid from the bacteria.

Method for Isolating Plasmid From the Bacteria

To digest the bacteria, 0.5 grams of cells were resuspended in eight-tenths of the final working volume of 50 mM TRIS buffer. One-tenth of the final working volume of TRIS buffer containing a sufficient amount of lysozyme for a final concentration of 2 milligrams per milliliter was added to the above solution. The solution was allowed to incubate without shaking in a water bath at 37° C. for an appropriate period, preferably between 30 minutes to one hour. After this incubation, EDTA was added to the solution to a final concentration of 20 mM along with pronase to a final concentration of 500 ug per ml and sodium dodecyl sulfate (SDS) in an amount sufficient to reach a 1% (w/v) final concentration. This solution was then incubated for an appropriate period, preferably about one-half hour in this example at about 37° C.

Following this digestion, the solution was rapidly denatured using 3N sodium hydroxide (NaOH) added to achieve a pH in the range between 12.1 to 12.4 and preferably from 12.1 to 12.2. The denatured solution was rapidly neutralized with an amount of 2 Molar TRIS HCl at a pH of 7.0 sufficient to bring the reaction mixture to a pH range of between 8 to 8.4. Sodium chloride was then added to a final concentration of 3% (w/v).

The solution was extracted one time in phenol followed by a further extraction with chloroform/isoamyl alchol in a ratio of approximately 24 to 1. Sodium acetate was added to the plasmid DNA containing fraction to a final concentration of approximately 300 mM sodium acetate. Two volumes of ethanol were added to this solution. A precipitate formed overnight at −20° C. was collected by centrifugation at approximately 10,000 times (X) gravity.

The precipitate was resuspended in a buffer of 50 mM TRIS, 20 mM EDTA, 100 mM sodium chloride at a pH of approximately 8. Sodium acetate was added to this solution to a final concentration of approximately 300 mM. Two volumes of ethanol were added to this solution and a precipitate was allowed to form for an appropriate period of time, preferably about 2 hour at −70° C. The plasmid was pelleted by centrifugation as above. The pellet was resuspended in 3.9 ml of Tris-EDTA-sodium chloride (TES) buffer containing 4.1 g of cesium chloride and 0.3 ml of ethidium bromide solution at a concentration of 10 mg per ml. The solution was centrifuged for a period of time and speed sufficient to form a cesium chloride equilibrium gradient, in this example at about 45,000X gravity overnight. Bands containing DNA were visualized with ultraviolet light and the band containing the plasmid DNA was extracted by mans of needle puncture of the tube. Other means of selectively removing the plasmid DNA band can be used with equal effectiveness. The plasmid DNA was further purified by resuspension in TES buffer containing cesium chloride and ethidium bromide and repeating the above centrifugation step.

Resolution of Plasmid

Plasmids were resolved by use of appropriate means, for example, running in a linear 5% to 20% sucrose gradient or loading the plasmid containing solution onto a 0.7% agarose gel and running the gel at an appropriate voltage to ensure resolution of the plasmid bands. In one embodiment, a 0.7% agarose gel is used. The separation of the bands is followed by means of a tracking dye containing bromophenyl blue, 2% sodium dodecyl sulfate (SDS), and 50% glycerol. The position of the separated bands is determined by staining with an ethidium bromide solution and viewing under ultraviolet light.

Agarose gel electrophoresis carried out as described above, indicate that *Cornebacterium glutamium* ATCC 39269 derived from ATCC 13058 has at least 3 plasmids. The first plasmid is approximately $2 \times 10^6$ daltons (d) in molecular weight and is approximately 3.1 kilobases (kb) in length. This plasmid is designated pRN3.1. The second plasmid is approximately $14.5 \times 10^6$ d and approximately 23.7 kb in length. The third plasmid is approximately $20 \times 10^6$ d and approximately 32.6 kb in length.

Once the various plasmid fractions are resolved, they are isolated by appropriate means. In the preferred method, the resolved fractions are removed by cutting the gel to form a well and electroeluting the plasmid fraction into a dialysis membrane. This method is well known in the art and is described in considerable detail in *Methods of Enzymology*, Vol. 65, (1980) pp. 319–327. The plasmid fractions eluted in this fashion are then extracted in phenol and precipitated in ethanol whereby the plasmid DNA is concentrated.

Characterization of *Cornebacterium glutamicum* Plasmids by Restriction Endonucleases Separate aliquots of the $2 \times 10^6$ d plasmid containing approximately 0.2 ug DNA as determined by the optical density of the solution at 260 nanometers in a spectrophotometer, was suspended in an excess of each of the following endonucleases and appropriate salts for each of the respective nucleases as determined by the manufacturer: Hind III, Bgl II, Kpn 1, Sal I, Hinf I, and Hae III. A double digest using Bgl II and Hind III was run under the following conditions. Two-tenths micrograms DNA was suspended in buffer containing an excess of Bgl II enzyme, and the appropriate salts for Bgl II restriction endonuclease as recommended by the manufacturer. The plasmid was digested for 45 minutes under these conditions with Bgl II. Thereafter, sodium chloride was added to the solution to a final concentration of 60 mM and an excess of Hind III restriction endonuclease was added to the solution. The solution was then incubated for 30 minutes at 37° C. The endonuclease digests of the plasmid were resolved by running on a 1% agarose gel or 5% acrylamide gel. Appropriate DNA standards were run along side the plasmid in DNA digests. The results are reported in the following table:

TABLE

| Restriction Enzyme | Cleavage sites | Fragment Size |
|---|---|---|
| Hind III | 2 | 2.85 kb; 0.245 |
| Bgl II | 1 | 3.2 kb |
| Kpn I | 0 | |
| Sal I | 0 | |
| Hinf I | >7 | |
| Hae III | >10 | |
| Bgl II + Hind III | 3 | 2.85 kb; 0.15 kb; 0.095 kb |

With respect to the relative locations of the Hind III and Bgl II sites, the 2.85 kilobase fragment is found in both the Hind III digestion and the combined Hind III/Bgl II digestion. This indicates that the Bgl II site is located within the smaller of the two Hind III fragments. Based on these data, the restriction map of this plasmid designated pRN3.1 illustrated in FIG. 1 has been proposed.

We claim:

1. An essentially pure plasmid pRN3.1 isolated from *Corynebacterium glutamicum*, characterized by a molecular weight of about $2 \times 10^6$ daltons and a plurality of cleavage sites for restriction endonucleases as follows:

| Restriction enzyme | Cleavage site |
|---|---|
| Hind III | 2 |
| Bgl II | 1 |

-continued

| Restriction enzyme | Cleavage site |
|---|---|
| Kpn I | 0 |
| Sal I | 0 |
| Hinf I | >7 |
| Hae III | >10. |

* * * * *